(12) United States Patent
D'Agostino et al.

(10) Patent No.: US 9,364,229 B2
(45) Date of Patent: Jun. 14, 2016

(54) CIRCULAR ANASTOMOSIS STRUCTURES

(75) Inventors: William L. D'Agostino, Mt. Carmel, CT (US); Michael Bettuchi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 1528 days.

(21) Appl. No.: 12/692,882

(22) Filed: Jan. 25, 2010

(65) Prior Publication Data

US 2010/0147923 A1    Jun. 17, 2010

Related U.S. Application Data

(63) Continuation-in-part of application No. 11/080,854, filed on Mar. 15, 2005, now Pat. No. 7,942,890, and a continuation-in-part of application No. 11/365,637, filed on Feb. 28, 2006, now abandoned.

(51) Int. Cl.
| | |
|---|---|
| *A61B 17/072* | (2006.01) |
| *A61B 17/115* | (2006.01) |
| *A61B 17/00* | (2006.01) |
| *A61B 17/11* | (2006.01) |

(52) U.S. Cl.
CPC ......... *A61B 17/072* (2013.01); *A61B 17/07292* (2013.01); *A61B 17/115* (2013.01); *A61B 17/00491* (2013.01); *A61B 17/1114* (2013.01); *A61B 17/1155* (2013.01); *A61B 2017/00004* (2013.01); *A61B 2017/00893* (2013.01)

(58) Field of Classification Search
USPC ......... 606/139, 151–153, 213–215, 219, 142; 227/175.1, 180.1
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 4,347,847 A | 9/1982 | Usher |
| 4,354,628 A | 10/1982 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,841,962 A | 6/1989 | Berg et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |

(Continued)

FOREIGN PATENT DOCUMENTS

| | | |
|---|---|---|
| DE | 1 99 24 311 | 11/2000 |
| DE | 1 99 24 311 A1 | 11/2000 |

(Continued)

OTHER PUBLICATIONS

International Search Report corresponding to European Application No. EP 10 25 0715.9, completed on Jun. 30, 2010 and mailed on Jul. 20, 2010; 3 pages.

(Continued)

*Primary Examiner* — Dianne Dornbusch

(57) ABSTRACT

The present disclosure provides annular support structures for use in conjunction with stapling devices. These annular support structures may be suitable for reducing occurrences of leaking, bleeding and/or stricture, as well as anastomotic tension, when anastomosing various body structures.

6 Claims, 5 Drawing Sheets

(56) References Cited

U.S. PATENT DOCUMENTS

| | | |
|---|---|---|
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,319,264 B1 | 11/2001 | Tormala et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,712,853 B2 | 3/2004 | Kuslich |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 7,147,138 B2 | 12/2006 | Shelton, IV |
| 7,404,819 B1 | 7/2008 | Darios et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,669,747 B2 | 3/2010 | Weisenburgh, II et al. |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0035401 A1 | 3/2002 | Boyce et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0009181 A1 | 1/2003 | Gellman et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2003/0212460 A1 | 11/2003 | Darois et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0210282 A1 | 10/2004 | Flock et al. |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |

(56) References Cited

U.S. PATENT DOCUMENTS

| | | |
|---|---|---|
| 2006/0271104 A1 | 11/2006 | Viola et al. |
| 2007/0026031 A1 | 2/2007 | Bauman et al. |
| 2007/0027472 A1 | 2/2007 | Hiles et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |

FOREIGN PATENT DOCUMENTS

| | | |
|---|---|---|
| DE | 199 24 311 A1 | 11/2000 |
| EP | 0 327 022 | 8/1989 |
| EP | 0 594 148 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 520 525 | 4/2005 |
| EP | 1 520 525 A1 | 4/2005 |
| EP | 1 621 141 A21 | 2/2006 |
| EP | 1 702 570 A1 | 9/2006 |
| EP | 1 759 640 A2 | 3/2007 |
| EP | 1 815 804 A2 | 8/2007 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 198 787 A1 | 6/2010 |
| EP | 2 236 098 A2 | 10/2010 |
| JP | 2000-166933 | 6/2000 |
| WO | WO 90/05489 | 5/1990 |
| WO | WO 90/05489 A1 | 5/1990 |
| WO | WO 96/22055 A1 | 7/1996 |
| WO | WO 97/01989 A1 | 1/1997 |
| WO | WO 97/13463 A1 | 4/1997 |
| WO | WO 98/17180 | 4/1998 |
| WO | WO 98/17180 A1 | 4/1998 |
| WO | WO 99/45849 | 9/1999 |
| WO | WO 99/45849 A1 | 9/1999 |
| WO | WO 03/082126 | 10/2003 |
| WO | WO 03/082126 A1 | 10/2003 |
| WO | WO 03/105698 A2 | 12/2003 |
| WO | WO 2006/023578 | 3/2006 |
| WO | WO 2006/023578 A2 | 3/2006 |
| WO | WO 2006/044490 | 4/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 10 25 0642.5, completed on Mar. 25, 2011 and mailed on Apr. 4, 2011; 4 pages.

International Search Report from Application No. EP 06016962.0 dated Jan. 3, 2007.

International Search Report from Application No. PCT/US05/36740 mailed Mar. 23, 2007.

International Search Report from Application No. PCT/US2008/002981 dated Jun. 26, 2008.

International Search Report from Application No. EP 08 25 1779 dated Jul. 23, 2008.

European Search Report from Application No. EP 060004598 dated Jun. 22, 2006.

International Search Report corresponding to European Application No. EP 06 00 4598, completed on Jun. 22, 2006; 2 pages.

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

(56) References Cited

OTHER PUBLICATIONS

International Search Report corresponding to European Application No. EP 08 25 1989.3, completed on Mar. 11, 2010 and mailed on Mar. 24, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

International Search Report corresponding to European Application No. EP 11 18 8309.6, completed on Dec. 15, 2011 and mailed on Jan. 12, 2012; 3 pages.

International Search Report corresponding to European Application No. EP 12 15 2229.6, completed on Feb. 23, 2012 and mailed on Mar. 1, 2012; 4 pages.

International Search Report corresponding to European Application No. EP 12 15 0511.9, completed on Apr. 16, 2012 and mailed on Apr. 24, 2012; 7 pages.

International Search Report corresponding to European Application No. EP 12 15 2541.4, completed on Apr. 23, 2012 and mailed on May 3, 2012; 10 pages.

International Search Report corresponding to European Application No. EP 12 16 5609.4, completed on Jul. 5, 2012 and mailed on Jul. 13, 2012; 8 pages.

International Search Report corresponding to European Application No. EP 12 15 8861.0, completed on Jul. 17, 2012 and mailed on Jul. 24, 2012; 9 pages.

International Search Report corresponding to European Application No. EP 12 16 5878.5, completed on Jul. 24, 2012 and mailed on Aug. 6, 2012; 8 pages.

CIRCULAR ANASTOMOSIS STRUCTURES

CROSS-REFERENCE TO RELATED APPLICATIONS

The present application is a Continuation-in-Part Application which claims the benefit of and priority to U.S. patent application Ser. No. 11/080,854, filed Mar. 15, 2005, now U.S. Pat. No. 7,942,890, the entire disclosure of which is incorporated herein by reference.

The present application is a Continuation-in-Part Application which claims the benefit of and priority to U.S. patent application Ser. No. 11/365,637, filed on Feb. 28, 2006, now abandoned the entire disclosures of which is incorporated herein be reference.

BACKGROUND

1. Technical Field

The present disclosure relates to surgical support structures and, more particularly, to adhesive support structures, gaskets, disks, and the like for use in conjunction with stapling devices, for reducing occurrences of leaking, bleeding and/or stricture, as well as anastomotic tension, when anastomosing various body structures.

2. Background of Related Art

Staples have traditionally been used to replace suturing when joining or anastomosing various body structures such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

In addition to the use of surgical staples, biological tissue adhesives have been developed for tissue repair and the creation of anastomoses. Generally, biological adhesives bond separated tissues together to aid in the healing process and to enhance tissue strength. Such adhesives may be used instead of suturing and stapling, for example, in surgical procedures for the repair of tissue or the creation of anastomoses.

Generally, following the formation of the anastomosis, a separate instrument or device is used to apply biological sealants to the outer surface of the anastomosis. Typically, in a separate step, the biological sealants are applied to the outer surface of the anastomosis by spraying, brushing, swabbing, any combinations thereof, or any other method contemplated by those skilled in the art. The biological sealants act to reduce and/or stop the incidents of leakage from the anastomosis.

The application of a suitable biocompatible adhesive offers many advantages to the patient and the surgeon alike, such as, for example, the possible reduction in the number of staples used, immediate sealing of the tissue being treated, a strengthening of the anastomosis, and a reduction in the occurrence of bleeding from the blood vessels, leakage through the tissue joint, and stricture. Moreover, use of biocompatible adhesives tends to minimize foreign body reaction and scarring.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. No. 5,392,979 to Green et al., and U.S. Pat. Nos. 5,799,857 and 5,915,616 to Robertson et al., the entirety of each of which is incorporated herein by reference.

In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

In some surgical operations, surgical supports, e.g., meshes, are employed by surgeons in combination with linear stapling devices to bridge, repair and/or reinforce tissue defects within a patient, especially those occurring in the abdominal wall, chest wall, diaphragm, and other musculo-aponeurotic areas of the body. Examples of suitable surgical supports are disclosed in U.S. Pat. Nos. 3,054,406, 3,124,136, 4,347,847, 4,655,221, 4,838,884 and 5,002,551, the entirety of each of which is incorporated herein by reference.

When the staples are applied in surgical procedures utilizing surgical supports (i.e., reinforcing material), the legs of the staple typically pass from the cartridge jaw through a layer of the surgical support, and through the patient's tissue before encountering the anvil jaw. In an alternative procedure, the legs of the staple typically pass from the cartridge jaw through a first layer of the surgical support, then through the patient's tissue, and finally through a second layer of the surgical support before encountering the anvil jaw. With the staples in place, the stapled tissue is clamped between the layers of the surgical support.

While the surgical supports described above are used in conjunction with linear surgical stapling devices, the need exists for improved support structures for use in conjunction with surgical stapling devices.

SUMMARY

The present disclosure provides annular structures for deposition between adjacent intestinal sections in an anastomosis procedure. According to an aspect of the present disclosure, an apparatus for forming an anastomosis between adjacent tissue sections is provided. The apparatus includes an anastomosis device including an anvil assembly having a shaft which is selectively attachable to a tubular body portion, wherein the tubular body portion includes at least one annular row of staples operatively disposed therein. The apparatus further includes a disk having an outer terminal edge, an inner portion aligned with the annular row of staples, and a substantially centrally located aperture. The outer terminal portion of the disk has an adhesive material and extends radially outward beyond the outer-most row of the at least one annular row of staples to adhesively attach the tissue sections together radially outward of the at least one annular row of staples and form a rim of adhered tissue around the annular row of deployed staples.

The present disclosure also provides methods for disposing an annular structure between adjacent intestinal sections. According to another aspect of the present disclosure, a method of performing an anastomotic procedure on adjacent tissue sections is provided. The method includes the steps of: a) providing a surgical stapling device including an anvil assembly and a body portion, the anvil assembly including an anvil member supported on an anvil shaft and the body portion carrying a plurality of surgical staples arranged in an annular row and a knife; and b) providing a disk having an outer terminal edge which extends radially outward beyond an outer-most row of the at least one annular row of staples, the disk having an adhesive material at the outer terminal portion.

The method may further includes the steps of: c) inserting the anvil assembly into a first tissue section; d) inserting the body portion into a second tissue section; e) disposing the disk between the first tissue section and the second tissue section, the disk having an outer terminal portion with an adhesive material; f) approximating the anvil assembly and body portion with one another so that the first tissue section, the second tissue section and the disk are disposed between the anvil assembly and the body portion, wherein the disk is interposed between the first tissue section and the second tissue section, and wherein the outer terminal edge of the disk extends radially outward beyond the outer-most row of the at least one annular row of staples; g) deploying the staples from the body portion; h) forming a rim of adhered tissue outwardly of the annular row of deployed staples; and i) cutting the first tissue section, the second tissue section, and the disk with the knife.

It is envisioned that the disk may be fabricated from at least one of a bioabsorbable and a non-bioabsorbable material.

The disk may include a material selected from the group consisting of an adhesive, a sealant, a hemostat, and a medicament.

The disk reduces the tension exhibited on the outer-most row of the at least one annular row of staples when the adjacent tissue sections are pulled away from one another.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 1A is a perspective view of a circular anastomosis structure in accordance with an embodiment of the present disclosure, for use with the annular surgical stapling device of FIG. 1;

DETAILED DESCRIPTION OF EMBODIMENTS

Figure 1:
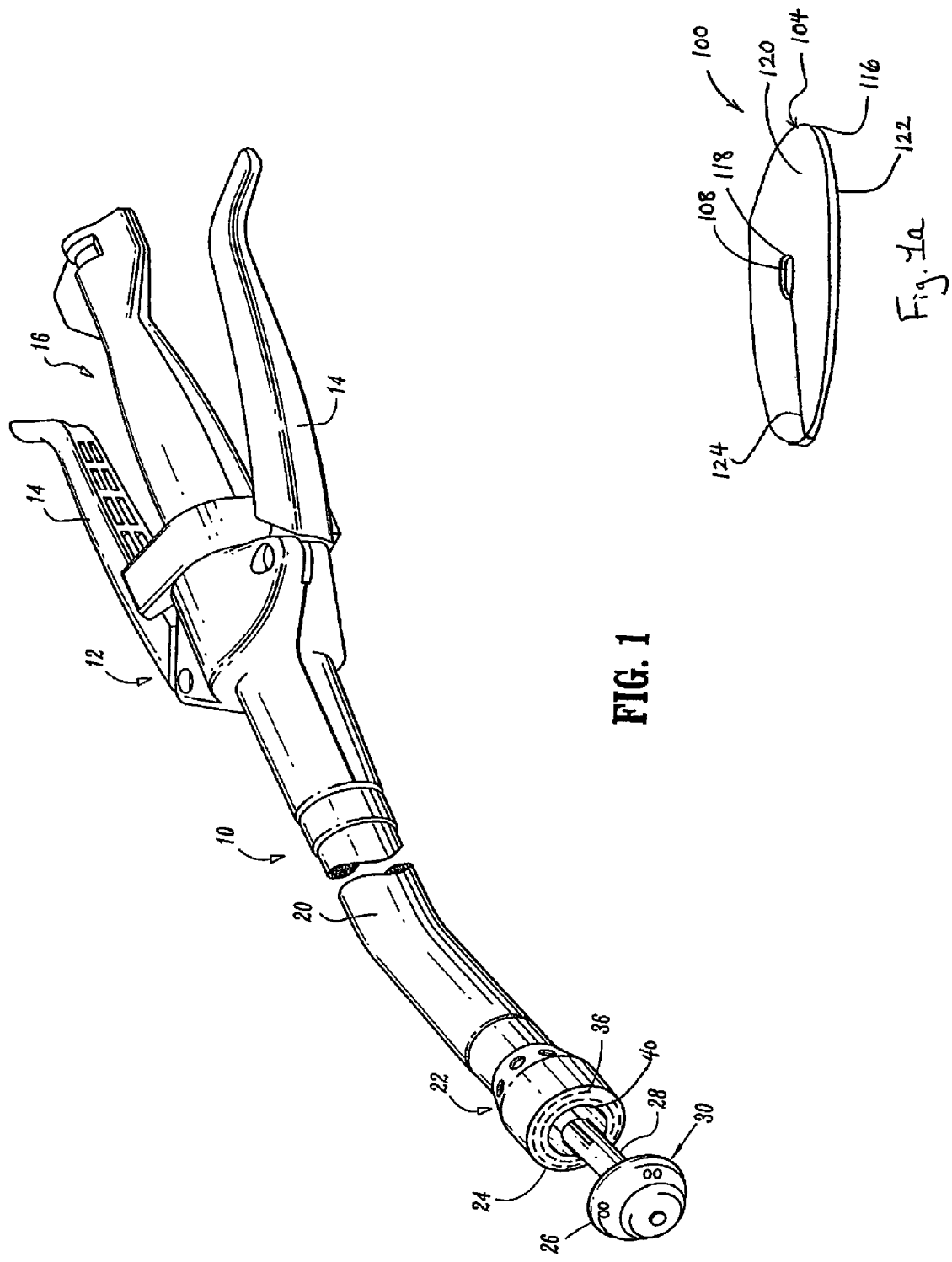
FIG. 1 is a perspective view of an exemplary annular surgical stapling device.

Embodiments of the presently disclosed circular anastomosis structures, also referred to herein as circular anastomosis gaskets or disks, will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Referring initially to FIG. 1, an annular surgical stapling device, for use with the circular anastomosis structures disclosed herein, is generally designated as 10. Surgical stapling device 10 includes a handle assembly 12 having at least one pivotable actuating handle member 14, and an advancing member 16. Extending from handle member 12, there is provided a tubular body portion 20 which may be constructed so as to have a curved shape along its length. Body portion 20 terminates in a staple cartridge assembly 22 which includes a pair of annular arrays of staple receiving slots 36 having a staple (not shown) disposed in each one of staple receiving slots 36. Positioned distally of staple cartridge assembly 22 there is provided an anvil assembly 30 including an anvil member 26 and a shaft 28 operatively associated therewith for removably connecting anvil assembly 30 to a distal end portion or connection member 40 of stapling device 10.

Staple cartridge assembly 22 may be fixedly connected to the distal end of tubular body portion 20 or may be configured to concentrically fit within the distal end of tubular body portion 20. Typically, staple cartridge assembly 22 includes a staple pusher (not shown) including a proximal portion having a generally frusto-conical shape and a distal portion defining two concentric rings of peripherally spaced fingers (not shown), each one of which is received within a respective staple receiving slot 36.

Typically, a knife (not shown), substantially in the form of an open cup with the rim thereof defining a knife edge, is disposed within staple cartridge assembly 22 and mounted to a distal surface of a staple pusher (not shown). The knife edge is disposed radially inward of the pair of annular arrays of staples. Accordingly, in use, as the staple pusher is advanced, the knife is also advanced axially outward.

Reference may be made to U.S. Pat. No. 5,915,616 to Viola et al., the entire contents of which are incorporated herein by reference, for a detailed discussion of annular stapling device 10.

An anastomosis structure, in accordance with the present disclosure, is shown generally in FIG. 1A. Structure 100 is an adhesive disk desirably having a shape corresponding to the arrays of staple receiving slots 36. The structure 100 may include a washer-like or gasket-like body portion 104 including a substantially centrally located aperture 108 formed therethrough. Structure 100 is defined by an outer terminal edge 116, an inner terminal edge 118 defining the size of aperture 108, an upper surface 120, and a bottom surface 122.

Figure 2:
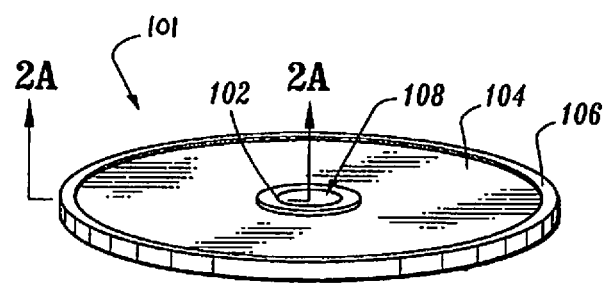
FIG. 2 is a perspective view of a circular anastomosis structure in accordance with another embodiment of the present disclosure, for use with the annular surgical stapling device of FIG. 1.
Figure 3:
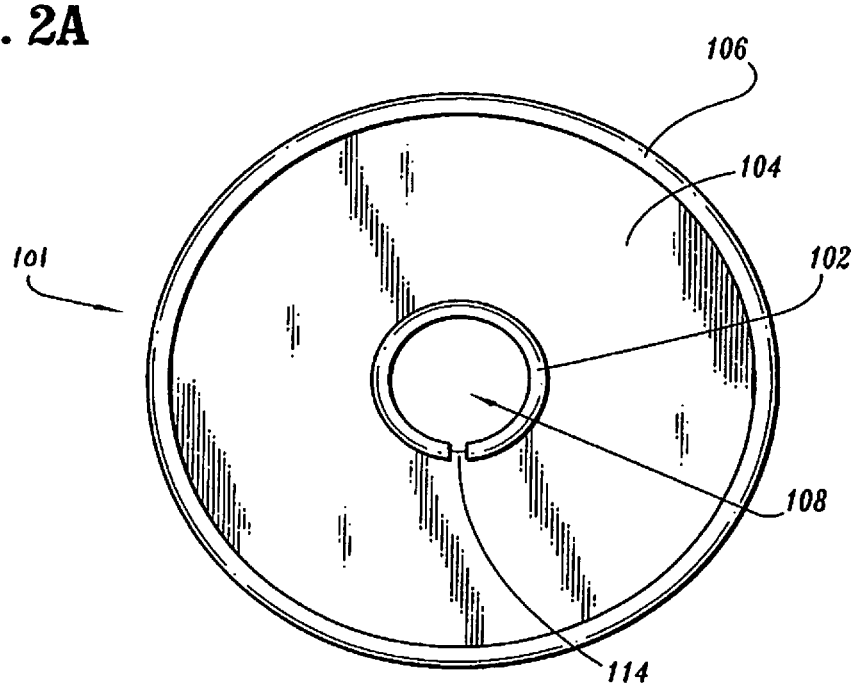
FIG. 3 is a top view of a circular anastomosis structure in accordance with yet another embodiment of the present disclosure, for use with the annular surgical stapling device of FIG. 1.

Turning now to FIGS. 2 and 3, an anastomosis structure, in accordance with another embodiment of the present disclosure, is generally designated as structure 101. Structure 101 includes an inner ring 102, a middle ring 104, and an outer ring 106. A substantially centrally located aperture 108, defined by the inner circumference of inner ring 102 is formed through structure 101.

In one embodiment, structure 100 is sized such that when structure 100 is operatively associated with stapling device 10, as will be described in greater detail below, outer terminal edge 116 extends radially beyond staple retaining pockets 36 of staple cartridge 22. In a similar manner, structure 101 may be sized such that when structure 101 is operatively associated with stapling device 10, outer ring 106 extends radially beyond staple retaining pockets 36 (see FIG. 1) of staple cartridge assembly 22. Additionally, aperture 108 of structure 100, 101 is sized to at least receive shaft 28 of anvil assembly 30 therethrough. In another embodiment, the distance between outer terminal edge 116 and inner terminal edge 118 of structure 100, and likewise the distance between outer ring 106 and inner ring 102 of structure 101, is substantially equal to a width of a tissue contact surface 24 (see FIG. 1) of staple cartridge assembly 22.

As seen in FIG. 3, circular anastomosis structure 101 includes at least two concentric rings. Where a three ring structure is utilized, as shown in FIGS. 2 and 3, structure 101 includes an inner ring 102, a middle ring 104, and an outer ring 106. Where a two ring structure is utilized (not shown), structure 101 includes a middle ring 104 and an outer ring 106. In this embodiment, inner ring 102 is missing and/or is otherwise optional.

It is contemplated that inner ring 102 may, in some embodiments, be made from non-absorbable materials including, but not limited to, both synthetic and natural materials, including polyolefins such as polypropylenes, nylon, and silk. Inner ring 102 may also be made of absorbable materials, including homopolymers, copolymers or blends obtained from one or more monomers selected from the group consisting of glycolide, glycolic acid, lactide, lactic acid, p-dioxanone, ε-caprolactone and trimethylene carbonate. In some embodiments inner ring 102 may be a composite of both non-absorbable and absorbable materials.

As seen in FIG. 3, in one embodiment the inner ring 102 may have one or more gaps 114 formed therein and/or therealong to help facilitate passage of inner ring 102 out of the patients' body and to help facilitate introduction of shaft 28 of anvil assembly 30 into aperture 108.

It is contemplated that body portion or middle ring 104 of structure 100, 101 may be fabricated from or include a surgical grade, biocompatible, non-absorbable (i.e., permanent) or absorbable (i.e., non-permanent) mesh or material desirably impregnated with an adhesive, sealant and/or other medicament. As used herein, "mesh" includes woven, knitted and braided materials. In addition, non-woven materials such as felts may be used. For example, middle ring 104 may be fabricated from "TEFLON", which is a registered trademark owned by DuPont de Nemours & Co. It is further contemplated that middle ring 104 may be fabricated from a biocompatible polymeric foam, felt, polytetrafluoroethylene (ePTFE), gelatin, fabric or the like, or any other biocompatible material.

Non-absorbable materials used for middle ring 104 include, but are not limited to, those that are fabricated from such polymers as polybutester, polyetherester, polyethylene, polypropylene, nylon, polyethylene terephthalate, polytetrafluoroethylene, polyvinylidene fluoride, and the like. Further non-absorbable materials which may be utilized include, but are not limited to, stainless steel, titanium and the like.

Bio-absorbable materials used for middle ring 104 of structure 100, 101 include, but are not limited to, those fabricated from homopolymers, copolymers or blends obtained from one or more monomers selected from the group consisting of glycolide, glycolic acid, lactide, lactic acid, p-dioxanone, ε-caprolactone and trimethylene carbonate. Other bio-absorbable materials include, but are not limited to, polyglycolic acid (PGA) and polylactic acid (PLA). In one embodiment, middle ring 104 may be fabricated from bio-absorbable felt, ePTFE, gelatin or any other bio-absorbable materials. In one particularly useful embodiment, polyglycolic acid (PGA) yarns may be used as the middle ring 104 of the circular anastomosis structure of the present disclosure. Suitable yarns include those sold in a mesh form as DEXON™ mesh by United States Surgical, a Division of Tyco Health-Care Group, LP, Norwalk, Conn.

Figure 2A:
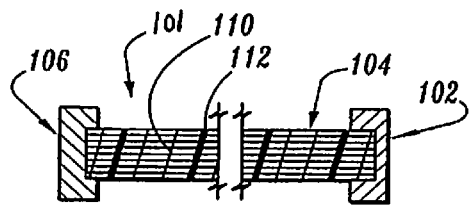
FIG. 2A is a cross-sectional view of the circular anastomosis structure of FIG. 2, as taken through 2A-2A of FIG. 2.

In one particularly useful embodiment, as seen in FIG. 2A, middle ring 104 can be made from a composite material made from a majority 110 of an absorbable yarn with a minority 112 of non-absorbable yarn, such as silk, cotton, nylon, polypropylene, polyester, polyethylene terephthalate, and the like. In some cases, it may be advantageous to include a minor portion of a non-absorbable yarn to increase tissue growth by enhancing tissue reactivity. While materials such as silk, cotton and nylon are classified by the FDA as non-absorbable materials, they will eventually break-down in the body, at a much slower rate than absorbable materials.

As with the inner ring 102, in some embodiments middle ring 104 may be a composite of both non-absorbable and absorbable materials.

Outer ring 108 may similarly be made of non-absorbable or absorbable materials described above for use in forming middle ring 104 or inner ring 102. In some embodiments, outer ring 108 may also be made from a composite of absorbable materials combining a knitted mesh such as DEXON™ mesh with an absorbable synthetic wax or synthetic sealant. For example, this absorbable material can be made from short-chain polymer(s) such as glycolide, lactide, trimethylene carbonate, dioxanone or the like, and any combinations thereof.

In a further embodiment, the structure has a middle ring and an inner ring and incorporates at least two different materials. The inner ring is formed from a non-bioabsorbable material, whereas the middle ring is formed from bio-absorbable materials and is preferably a compressible material arranged to be compressed between adjacent tissue sections so as to form a seal. The inner ring is desirably arranged so as to be at least partially removed by the circular knife of the stapling device and/or passed from the body.

As noted above, in some embodiments a minor portion of a non-absorbable material may also be incorporated into inner ring 102, outer ring 106, or both.

Figure 4:
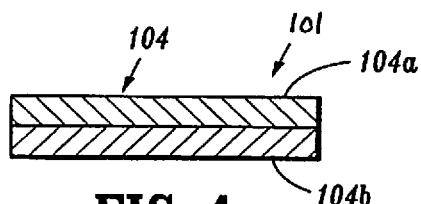
FIG. 4 is a cross-sectional view of a circular anastomosis structure in accordance with an alternate embodiment of the present disclosure for use with the annular surgical stapling device of FIG. 1.
Figure 5:
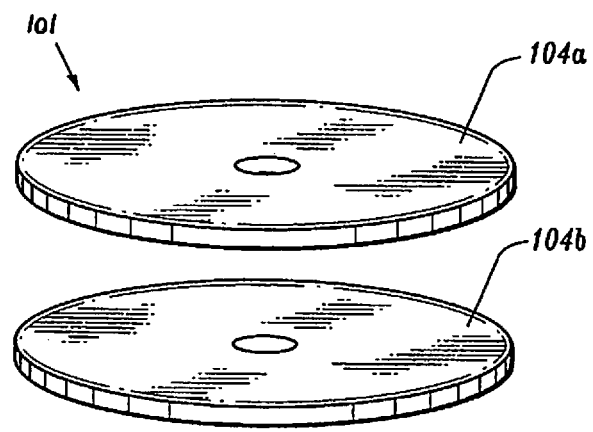
FIG. 5 is a perspective view of the circular anastomosis structure of FIG. 4 with parts separated.

In yet another embodiment, as seen in FIGS. 4 and 5, middle ring 104 can be made from a sandwich of composite materials including an upper layer 104a and a lower layer 104b. Desirably, layers 104a, 104b may be a knitted mesh made from both absorbable and non-absorbable yarns and include a sealant as a middle layer to secure layers 104a, 104b to one another. Sealants which may be utilized to adhere the upper and lower layers 104a, 104b of the middle ring 104 are known to those skilled in the art and include, but are not limited to, hydrogels, fibrin-based sealants, thrombin-based sealants, collagen-based sealants, and synthetic polymer sealants including those based on polyalkylene oxides such as polyethylene glycol, polydioxanones, polylactides, polyglycolides, and polycaprolactones. In one particularly useful embodiment, the sealant utilized to adhere the upper and lower layers 104a, 104b of middle ring 104 is an absorbable sealant which swells after contact with water, e.g., a hydrogel, which is analogous to a "foam in place" sealant.

In yet another embodiment, the multi-layer composite mesh utilized to form the middle ring 104 could be pre-impregnated (i.e., coated) with the swelling absorbable sealant.

In one embodiment, middle ring 104 of structure 100, 101 may be fabricated from a bio-absorbable material which is desirably impregnated with an adhesive, sealant, and/or other medicament (i.e., wound treatment material). Accordingly, in use, the sealant component of structure 100, 101 functions to retard any bleeding which may occur from the tissue, the adhesive component of structure 100, 101 functions to help secure the approximated tissue together, and the bio-absorbability of structure 100, 101 allows for at least a portion of structure 100, 101 to be absorbed into the body after a predetermined amount of time. For example, structure 100, 101 may remain in place in the body for approximately 2-3 weeks in order for the anastomosis to sufficiently heal prior to structure 100, 101 being absorbed into the body. In other embodiments, structure 100, 101 has at least one portion that is absorbable and at least one portion that is not absorbable.

Where utilized, the adhesive should be a biocompatible adhesive including, but not limited to, adhesives which cure upon tissue contact, which cure upon exposure to ultraviolet (UV) light, which are two-part systems kept isolated from one another and cure upon coming into contact with one another, which are pressure sensitive, which are any combinations thereof, or any other known suitable adhesive. In one embodiment, it is contemplated that an adhesive having a cure time of from about 10 to about 15 seconds may be used. In another embodiment, it is contemplated that an adhesive having a cure time of about 30 seconds may be used.

It is envisioned that middle ring 104 of structure 100, 101 may be impregnated with a pre-cured adhesive or sealant. The pre-cured sealant or adhesive will react with the moisture and/or heat of the body tissue to thereby activate the sealing and/or adhesive properties of the sealant or adhesive. Thus, in one embodiment the pre-cured sealant or adhesive may be a hydrogel or the like.

It is envisioned that the adhesive may be utilized alone or combined with one or more other wound treatment materials. The wound treatment material includes and is not limited to one or a combination of adhesives, hemostats, sealants, coagulants, astringents, and medicaments. Other surgically biocompatible wound treatment materials which may be employed in or applied by surgical instruments, especially surgical staplers utilized to repair tissue and create anastomosis with the anastomosis composite structure herein, include adhesives whose function is to attach or hold organs, tissues or structures; sealants to prevent fluid leakage; hemostats to halt or prevent bleeding; and medicaments.

Examples of additional adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants which can be employed include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc.

Examples of hemostat materials which can be employed include fibrin-based, collagen-based oxidized regenerated cellulose-based, and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein also include astringents, e.g., aluminum sulfate, and coagulants.

The wound treatment material may include a cross-linking material and/or reactive agent that reacts with the support structure, tissue or both. The resulting material acts as a seal or tissue-joining material that is non-absorbable. For example, the wound treatment material may be based on biocompatible cross-linked polymers formed from water soluble precursors having electrophilic and nucleophilic groups capable of reacting and cross-linking in situ, including those disclosed in U.S. Pat. No. 6,566,406, the entire contents of which are incorporated herein by reference.

The wound treatment material may include visco-elastic film forming materials, cross-linking reactive agents, and energy curable adhesives. It is envisioned that wound treatment material, and in particular, adhesive may be cured with the application of water and/or glycerin (e.g., 1,2,3-pranatetriol, also known as glycerol and glycerine) thereto. In this manner, the water and/or glycerin cure the adhesive and hydrate the wound.

The term "medicament", as used herein, is used in its broadest sense and includes any substance or mixture of substances that have clinical use. Consequently, medicaments may or may not have pharmacological activity per se, e.g., a dye. Alternatively a medicament could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of classes of medicaments which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of medicaments may be used.

Suitable antimicrobial agents which may be included as a medicament in the circular anastomosis structure of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a medicament in the circular anastomosis structure of the present disclosure.

Other medicaments which may be included in the circular anastomosis structure of the present disclosure include: local anesthetics; non-steroidal antifertility agents; parasympathomimetic agents; psychotherapeutic agents; tranquilizers; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable medicaments which may be included in the circular anastomosis structure of the present disclosure include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

It is further contemplated that medicaments may include, for example, compositions and/or compounds which accelerate or beneficially modify the healing process when particles of the composition and/or compound are applied to or exposed to a surgical repair site. For example, the medicament may be a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, medicament may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

A single medicament may be utilized in the circular anastomosis structure of the present disclosure or, in alternate embodiments, any combination of medicaments may be utilized in the circular anastomosis structure of the present disclosure.

The medicament may be disposed on a surface of structure 100, 101 or impregnated into structure 100, 101. The medicament may include one or more medically and/or surgically useful substances such as drugs, enzymes, growth factors, peptides, proteins, dyes, diagnostic agents or hemostatic agents, or any other pharmaceutical used in the prevention of stenosis.

In one embodiment, it is contemplated that middle ring 104 of structure 100, 101 may be impregnated with a first component of a two-part adhesive and that the device deploys the second component of the two-part adhesive. For example, in a surgical stapler 10, the staples, which are retained in staple receiving slots 36 of staple cartridge assembly 22, may be coated with a second component (e.g., a reactant) of the two-part adhesive. In this manner, the first component of the adhesive is activated when the staples penetrate and capture middle ring 104 of structure 100, 101 during the firing sequence of surgical stapling device 10, and the two components of the adhesive contact one another.

As seen in FIG. 3, structure 101 may include a single layered middle ring 104 including a homogeneous array of bio-absorbable or non-absorbable materials or a heterogeneous array or bio-absorbable and/or non-absorbable materials. Structure 100 may also be single layered and include a homogeneous array of bio-absorbable and/or non-absorbable materials.

In an alternate embodiment, it is contemplated that structure 100, 101 may be layered, i.e., having at least two layers. In this embodiment, each layer may include a homogeneous or heterogeneous array of bio-absorbable and/or non-absorbable materials. It is envisioned that each layer may be separated from one another prior to the surgical procedure. As seen in FIGS. 4 and 5 and as discussed above, structure 101 may include at least a dual layered middle ring 104 as indicated by first layer, film or wafer 104a and second layer, film or wafer 104b. In this embodiment, each layer 104a, 104b may include a homogeneous or heterogeneous array of bio-absorbable and/or non-absorbable materials. It is envisioned that each layer 104a, 104b may be separated from one another, as seen in FIG. 5, prior to the surgical procedure.

As will be described in greater detail below, first layer 104a of structure 100 may be placed against a surface of a first tissue to be anastomosed, in juxtaposition to a second tissue to be anastomosed, and second layer 104b of structure 100 may be placed against a surface of the second tissue to be anastomosed, in juxtaposition to the first tissue to be anastomosed. In this manner, as the first and second tissues are brought into contact with one another, first and second layers 104a, 104b of structure 100 are brought into contact with one another and allowed to mix and/or react. For example, first layer 104a of structure 100 may include a first component of a two-part adhesive or sealant while second layer 104b of structure 100 may include a second component of the two-part adhesive or sealant. Accordingly, in use, when first layer 104a and second layer 104b come into contact with one another, the first and second components of the two-part adhesive or sealant will also come into contact and mix thereby forming the adhesive or sealant.

First and second layers 104a and 104b may be fabricated as bio-absorbable film-like membranes which activate upon contact with one another and/or contact with a fluid (e.g., water, saline, blood, an activating fluid, etc.). It is envisioned that a break-away or tear-away divider or barrier (not shown) may be positioned between first and second layers 104a, 104b in order to prevent accidental and/or premature contact between first and second layers 104a and 104b. It is further envisioned that each first and second layer 104a and 104b may include a liner (not shown) removably disposed on at least one of a top or bottom surface thereof. In any of these embodiments, prior to contact of first and second layers 104a and 104b with one another, the divider and/or liners must be removed in order for activation of the adhesive to occur.

It is further envisioned that middle ring 104 of structure 100, 101 may be impregnated with a pressure sensitive adhesive which is activated when the adjacent layers of tissue are approximated. Suitable pressure sensitive adhesives are known to those skilled in the art and include, for example, acrylate polymers, and methacrylate polymers. In some embodiments, the pressure sensitive adhesive may be an alkyl methacrylate including, but not limited to, alkyl methacrylates containing 1 to about 10 carbon atoms in the alkyl group. Representative examples of suitable alkyl methacrylates include methyl methacrylate, n-butyl methacrylate, n-pentyl methacrylate, n-hexyl methacrylate, isoheptyl methacrylate, cyclohexyl methacrylate, n-nonyl methacrylate, n-decyl methacrylate, isohexyl methacrylate, 2-ethyloctyl methacrylate, isooctyl methacrylate, isobornyl methacrylate, 2-ethylhexyl methacrylate, and mixtures and combinations of the foregoing. Typically, the alkyl methacrylate may be isooctyl methacrylate, butyl methacrylate, 2-ethylhexyl methacrylate, cyclohexyl methacrylate, isobornyl methacrylate, and/or methyl methacrylate.

In some embodiments, the pressure sensitive adhesive may be a copolymer including an alkyl methacrylate described above copolymerized with one or more methacrylate monomers having at least one functional group selected from the grouping consisting of carboxylic acid, carboxylic acid ester, hydroxyl, anydride, epoxy, thiol, isocyanate, sulfonamide, urea, carbamate, carboxamide, amine, ammonium, oxy, oxo, nitro, nitrogen, sulfur, phosphate, phosphonate, cyano, combinations of these, and the like. Representative examples of specific materials that can be used singly or in combination as the methacrylate monomer having at least one functional group include methacrylic acid, maleic acid, vinyl acetate, a hydroxyalkyl methacrylate containing about 2 to about 4 carbon atoms in the hydroxyalkyl group, methacrylamide, an alkyl substituted methacrylamide having 1 to about 8 carbon atoms in the alkyl group, diacetone methacrylamide, a dialkyl methacrylamide independently having 1 or 2 carbon atoms in each alkyl group, N-vinyl-N-methyl acetamide, N-vinyl lactams, N-vinyl valerolactam, N-vinyl caprolactam, N-vinyl-2-pyrrolidone, glycidyl methacrylate, alkoxy methacrylate containing 1 to 4 carbon atoms in the alkoxy group, 2-ethoxyethyl methacrylate, 2,2-ethoxyethoxyethyl methacrylate, furfuryl methacrylate, tetrahydrofurfuryl methacrylate, propylene glycol monomethacrylate, polyethylene glycol methacrylate, polyethylene glycol methyl ether methacrylate, polyethylene oxide methyl ether methacrylate, di(lower)alkylaminopropyl methacrylamide (wherein lower means the alkyl moiety has 1 to 4 carbon atoms), methacrylonitrile, combinations of these, and the like. Typically, the copolymerizable monomer having at least one functional group include may be hydroxyethyl acrylate, hydroxyethyl methacrylate, acrylamide, glyceryl acrylate, N,N-dimethyl acrylamide, 2-ethoxyethyl acrylate, 2,2-ethoxyethoxyethyl acrylate, tetrahydrofurfuryl acrylate, vinyl acetate, and/or acrylic acid. Any of the aforementioned alkyl groups may be linear, branched or cyclic.

Figure 6:
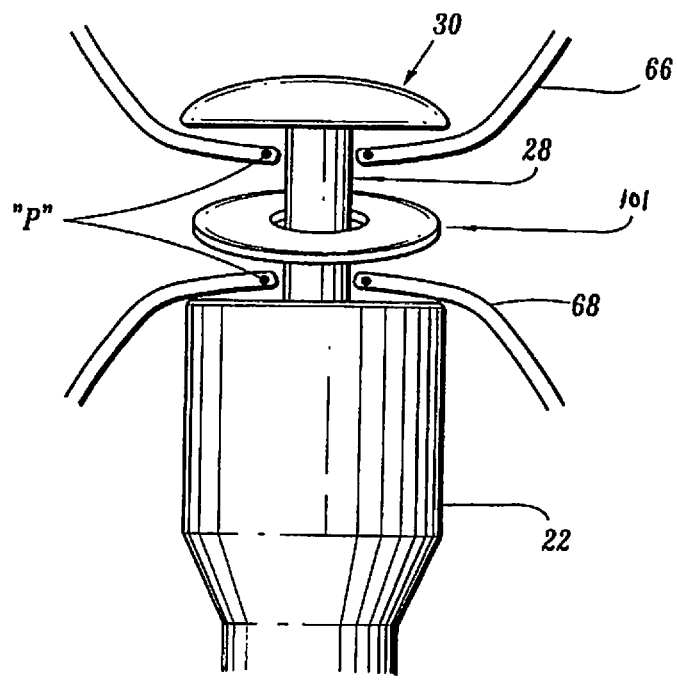
FIG. 6 is a side elevational view of the circular anastomosis structure of FIG. 5, illustrated in position on the annular surgical stapling device of FIG. 1.

As seen in FIG. 6, in use structure 101 may be placed such that aperture 108 receives shaft 28 of anvil assembly 30 therethrough and is at least substantially axially aligned with staple receiving slots 36 (see FIG. 1) of cartridge assembly 22.

Figure 7:
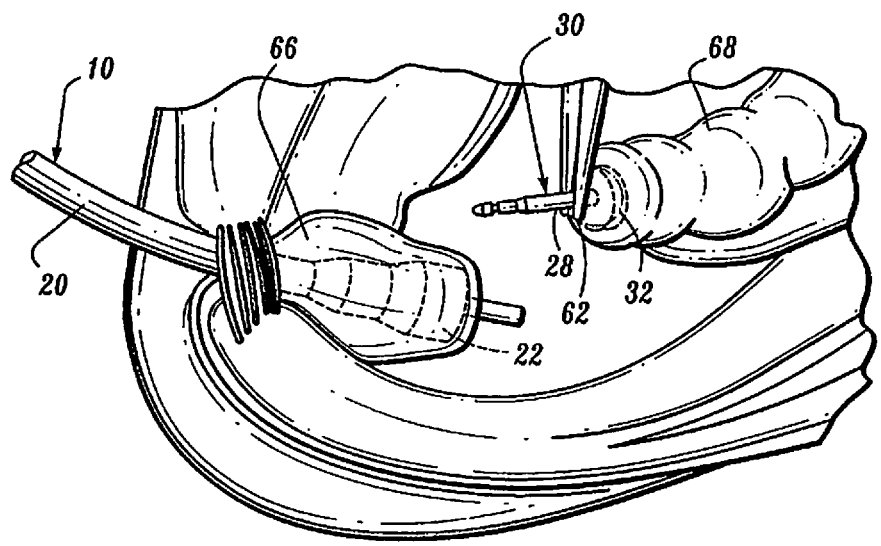
FIG. 7 is a perspective view of the intestinal area of a patient, illustrating a method of positioning a circular anastomosis structure of the present disclosure on the anvil rod of the annular stapling device of FIG. 1.
Figure 8:
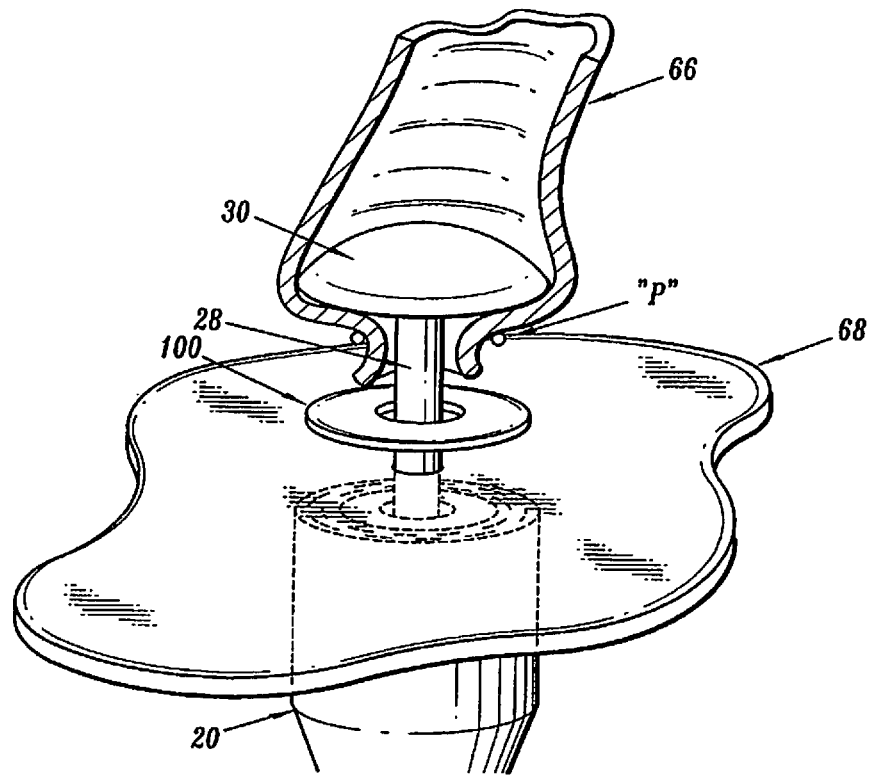
FIG. 8 is a schematic perspective view of the intestinal area of FIG. 7, illustrating the anvil rod mounted to the annular stapling device and having a circular anastomosis structure of the present disclosure disposed therebetween.

Turning now to FIGS. 7 and 8, there is illustrated the use of surgical stapling device 10 and detachable anvil assembly 30 in an anastomosis procedure to effect joining of intestinal sections 66 and 68. The anastomosis procedure is typically performed using minimally invasive surgical techniques including laparoscopic means and instrumentation. At the point in the procedure shown in FIG. 7, a diseased intestinal section has been previously removed, anvil assembly 30 has been applied to the operative site either through a surgical incision or transanally and positioned within intestinal section 68, and tubular body portion 20 of surgical stapling device 10 has been inserted transanally into intestinal section 66. Intestinal sections 66 and 68 are also shown temporarily secured about their respective components (e.g., shaft 28 of anvil assembly 30, and the distal end of tubular body portion 20) by conventional means such as a purse string suture "P" (see FIG. 8).

According to one method, as seen in FIG. 8, if desired or if the surgical procedure requires, circular anastomosis structure 100 or 101 may be placed onto shaft 28 of anvil assembly 30 prior to the coupling of anvil assembly 30 to the distal end of tubular body portion 20 in order for structure 100 or 101 to be located between intestinal sections 66 and 68. In particular, shaft 28 of anvil assembly 30 is inserted through aperture 104 of structure 100 or 101. In this position, structure 100 or 101 is located adjacent intestinal section 68. Following positioning of structure 100 or 101 onto shaft 28 of anvil assembly 30, the surgeon maneuvers anvil assembly 30 until the proximal end of shaft 28 is inserted into the distal end of tubular body portion 20 of surgical stapling device 10, wherein the mounting structure (not shown) within the distal end of tubular body portion 20 engages shaft 28 to effect the mounting.

Thereafter, anvil assembly 30 and tubular body portion 20 are approximated to approximate intestinal sections 66, 68 and capture circular anastomosis structure 100 or 101 therebetween. Surgical stapling device 10 is then fired thereby stapling intestinal sections 66, 68 to one another and cutting the portion of tissue and structure 100 or 101 disposed radially inward of the knife, to complete the anastomosis. Structure 100 may then release the adhesive impregnated therein to thereby adhere intestinal sections 66 and 68 to one another.

In the event that a structure 100 or 101 having a first and second layer 104a and 104b, each including one part of a two-part adhesive composition, is used, it is envisioned that first and second layers 104a and 104b are maintained separated and/or isolated from one another until approximation and firing of the surgical stapling device is to occur. Accordingly, in use, one of first and second layers 104a, 104b may be placed on shaft 28 of anvil assembly 30, against the surface of intestinal section 68, while the other of first and second layers 104a, 104b is placed against the surface of intestinal section 66. It is envisioned that pins (not shown) may extend distally from the distal end of tubular body portion 20 and penetrate through intestinal section 66. In this manner, the other of first and second layers 104a, 104b may be pinned onto the pins extending through intestinal section 66.

Alternatively, if a structure 100 or 101, having a first and second layer 104a and 104b, each including one part of a two-part adhesive composition, is used, it is envisioned that that each layer 104a, 104b may be provided with a tear-away or removable liner for maintaining first and second layers 104a, 104b separated and/or isolated from one another. Accordingly, both first and second layers 104a, 104b may be placed on shaft 28 of anvil assembly 30.

If a structure 100 or 101, having a first and second layer 104a, 104b, each including one part of a two-part adhesive composition, is used, the adhesive composition is activated upon first and second layers 104a, 104b coming into contact with one another.

Figure 9:
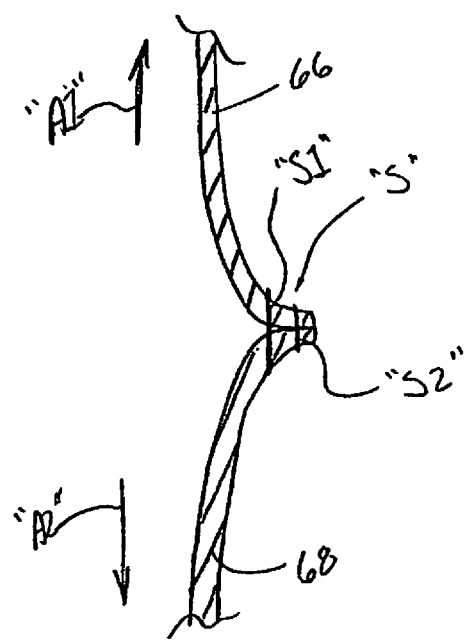
FIG. 9 is a cross-sectional schematic illustration of a pair of adjacent tissue sections joined to one another pursuant to a prior art anastomotic procedure, and exhibiting tension therebetween and on the resulting staple line.

Turning now to FIG. 9, a cross-sectional schematic illustration of a pair of adjacent tissue sections 66, 68 (i.e., intestinal sections), joined to one another with annular stapling device 10 according to the method described above, is shown.

As seen in FIG. 9, when tissue sections 66 and 68 undergo a degree of tension (i.e., being pulled in opposite directions from one another), as evidenced by arrows "A1, A2", a degree of mechanical strain is placed upon staples "S". A greater degree of strain is exhibited on the radially outwardly disposed staples "S1" as compared to the radially inward disposed staples "S2". In other words, as tissues sections 66 and 68 are pulled apart, in the direction of arrows "A1, A2", a relatively high degree of strain is placed on outer staples "S1" and then on inner staples "S2". Additionally, stress concentrations are formed and/or exhibited at each outer staple "S1" of the outer row of staples.

Figure 10:
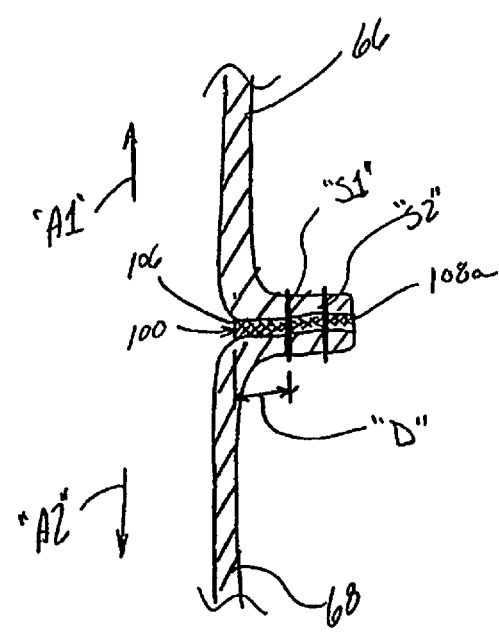
FIG. 10 is a cross-sectional schematic illustration of the pair of adjacent tissue sections of the intestinal area of FIGS. 7 and 8, joined to one another pursuant to a method of the present disclosure, and exhibiting a reduction of tension therebetween and on the resulting staple line.

As seen in FIG. 10, a cross-sectional schematic illustration of a pair of adjacent tissue sections 66, 68 joined to one another with annular stapling device 10 is shown with structure 100 or 101 captured therebetween. Outer terminal edge 116 of structure 100, or outer ring 106 of structure 101, extends radially outward, a distance "D", beyond the outer-most row of staples "S1" with structure 100 or 101 captured between tissue sections 66, 68. It is envisioned that anvil assembly 30 and tubular body portion 20 are maintained in the approximated condition for a time sufficient for that portion of structure 100 or 101 located radially outward of the outer-most row of staples "S1" to adhere and/or bond with each intestinal section 66 and 68. Moreover, as shown, following cutting of the knife through structure 100 or 101, a new inner terminal edge 108a is defined.

Any tension which may be experienced by intestinal sections 66 and 68, as illustrated by arrows "A1, A2" directed in opposite directions from one another, is initially absorbed by structure 100 or 101 in the location radially outward of the outer-most row of staples "S1". In this manner, the degree of strain exhibited on the outer-most row of staples "S1" is reduced as compared to when no structure 100 or 101 is present between intestinal sections 66 and 68. In other words, as intestinal sections 66 and 68 are pulled apart, in the direction of arrows "A1, A2", a relatively low degree of strain is placed on the outer-most row of staples "S1" and an even lower degree of strain is placed on the inner-most row of staples "S2". Additionally, stress concentrations at each outer staple "S1" of the outer row of staples is reduced by the inclusion of structure 100 or 101 between intestinal sections 66 and 68.

It is envisioned and understood that the greater the distance "D" that structure 100 or 101 extends beyond the outer-most row of staples "S1", the less the degree of strain which is placed on the outer-most row of staples "S1".

As seen in FIG. 1a, it is contemplated that structure 100 may include a slit 124 extending between inner terminal edge 118 and outer terminal edge 116 thereby enabling structure 100 to be positioned between intestinal sections 66 and 68 following connection of anvil assembly 30 and tubular body portion 20 of surgical stapling device 10.

From the foregoing, it will be appreciated that the circular anastomosis structures of the present disclosure function to strengthen the anastomosis and reduce the occurrence of bleeding, leaking and stricture, as well as anastomotic tension. It is also to be appreciated that the circular anastomosis structures of the present disclosure may be utilized in a number of other applications and is not limited solely to bowel or bronchus anastomosis.

Each circular anastomosis structure described above is constructed to enhance the formation of an anastomosis at the target surgical site. In some embodiments, the circular anastomosis structure may also be used to deliver an adhesive to the surgical site. The amount of adhesive to be delivered is site specific. Accordingly, different sized (e.g., different thickness or different volume) circular anastomosis structures are contemplated for retaining a different volume or quantity of adhesive therein. In this manner, depending on the particular need and the particular surgical procedure, the surgeon may select a circular anastomosis structure containing the needed and/or desired volume or quantity of adhesive therein.

While several particular forms of the circular anastomosis structures have been illustrated and described, it will also be apparent that various modifications can be made without departing from the spirit and scope of the present disclosure. For example, it is envisioned and within the scope of the present disclosure for an ultraviolet light activated adhesive to be used in connection with any of the circular anastomosis structures described above. In use, either prior to or following firing of surgical stapling device 10, the circular anastomosis structure is irradiated with UV light to thereby activate the adhesive.

It should be understood that features described and shown in one embodiment of an anastomotic structure of the present disclosure may be utilized in another embodiment of an anastomotic structure. For example, the composite materials including an upper layer and a lower layer shown in structure 101 may be utilized in structure 100. Similarly, the slit shown in structure 100 may be utilized with structure 101.

It is further contemplated that each of the circular anastomosis structures described herein may be used with an annular surgical anastomosing device, not including any staples for securing tissue together, which is capable of approximating, adhering and cutting tissue.

Thus, it should be understood that various changes in form, detail and application of the circular anastomosis structures of the present disclosure may be made without departing from the spirit and scope of the present disclosure.

What is claimed is:

1. An apparatus for forming an anastomosis between adjacent tissue sections, the apparatus comprising:
 a) an anastomosis device including an anvil assembly having a shaft which is selectively attachable to a tubular body portion, wherein the tubular body portion includes at least one annular row of staples operatively disposed therein; and b) a continuous disk having an outer terminal portion, an inner portion aligned with the annular row of staples, and a substantially centrally located aperture defined by the inner portion and dimensioned to receive the shaft of the anvil assembly, the disk being impregnated with an adhesive wound closure material at the outer terminal portion, wherein the outer terminal portion of the disk extends radially outward beyond an outer-most row of the at least one annular row of staples to adhesively attach the tissue sections together radially outward of the at least one annular row of staples and form a rim of adhered tissue around the annular row of deployed staples.

2. The apparatus according to claim 1, wherein the disk is fabricated from at least one of a bioabsorbable and a non-bioabsorbable material.

3. The apparatus according to claim 2, wherein the disk comprises a material selected from the group consisting of an adhesive, a sealant, a hemostat, and a medicament.

4. The apparatus according to claim 1, wherein the disk reduces the tension exhibited on the outer-most row of the at least one annular row of staples when the adjacent tissue sections are pulled away from one another.

5. The apparatus according to claim 1, wherein the adhesive material is dispersed throughout the disk.

6. The apparatus according to claim 1, wherein the inner portion of the disk is a mesh.

* * * * *